United States Patent
Matsui

(10) Patent No.: US 11,851,701 B2
(45) Date of Patent: Dec. 26, 2023

(54) OLIGONUCLEOTIDE PROBE FOR DETECTING SINGLE NUCLEOTIDE POLYMORPHISMS, AND METHOD FOR DETERMINING CIS-TRANS CONFIGURATION

(71) Applicant: EIKEN KAGAKU KABUSHIKI KAISHA, Tokyo (JP)

(72) Inventor: Atsuka Matsui, Tochigi (JP)

(73) Assignee: EIKEN KAGAKU KABUSHIKI KAISHA, Tokyo (JP)

(*) Notice: Subject to any disclaimer, the term of this patent is extended or adjusted under 35 U.S.C. 154(b) by 172 days.

(21) Appl. No.: 16/980,367

(22) PCT Filed: Mar. 12, 2019

(86) PCT No.: PCT/JP2019/010012
§ 371 (c)(1),
(2) Date: Sep. 11, 2020

(87) PCT Pub. No.: WO2019/176939
PCT Pub. Date: Sep. 19, 2019

(65) Prior Publication Data
US 2021/0040544 A1 Feb. 11, 2021

(30) Foreign Application Priority Data
Mar. 15, 2018 (JP) ................. 2018-047582

(51) Int. Cl.
*C12Q 1/6827* (2018.01)
*C12Q 1/6876* (2018.01)

(52) U.S. Cl.
CPC ......... *C12Q 1/6827* (2013.01); *C12Q 1/6876* (2013.01)

(58) Field of Classification Search
CPC .. C12Q 1/6827; C12Q 1/6876; C12Q 1/6886; C12Q 2600/156; C12Q 2525/161; C12Q 2535/131; C12Q 2563/107; C12Q 2525/197; C12N 15/09
See application file for complete search history.

(56) References Cited

U.S. PATENT DOCUMENTS

| | | | |
|---|---|---|---|
| 2003/0165925 A1 | 9/2003 | Saito et al. | |
| 2004/0152118 A1 | 8/2004 | Van Atta et al. | |
| 2012/0214166 A1 | 8/2012 | Ijuin | |
| 2014/0227683 A1* | 8/2014 | Cobb | C12Q 1/6827 435/5 |
| 2015/0064696 A1 | 3/2015 | Takoh | |
| 2016/0281166 A1* | 9/2016 | Bhattacharjee | G16B 35/00 |
| 2017/0342471 A1 | 11/2017 | Michiyuki | |
| 2019/0008986 A1 | 1/2019 | Butler et al. | |

FOREIGN PATENT DOCUMENTS

| | | |
|---|---|---|
| CN | 101074450 A | 11/2007 |
| CN | 101765665 A | 6/2010 |
| CN | 105189308 A | 12/2015 |
| CN | 107109398 A | 8/2017 |
| CN | 107488710 A | 12/2017 |
| CN | 107083438 * | 8/2022 |
| JP | 2001286300 A | 10/2001 |
| JP | 2009517054 A | 4/2009 |
| JP | 2012523821 A | 10/2012 |
| JP | 2014526257 A | 10/2014 |
| WO | 2004/000995 A2 | 12/2003 |
| WO | 2006/086777 A2 | 8/2006 |
| WO | 2007/062486 A1 | 6/2007 |
| WO | 2010/111682 A2 | 9/2010 |
| WO | 2011/052754 A1 | 5/2011 |
| WO | 2013/041853 A1 | 3/2013 |
| WO | 2013/145939 A1 | 10/2013 |
| WO | 2015/071552 A1 | 5/2015 |
| WO | WO-2016098595 A1 * | 6/2016 ............. C12N 15/09 |

OTHER PUBLICATIONS

CN 107083438 Machine Translation in English, 2017, Primer, Probe and Method for Detecting EGFR Gene 20 Exon T790M and C797S Mutation, Published Aug. 12, 2022, 10 pgs. (Year: 2017).*
Patent Cooperation Treaty, International Preliminary Report on Patentability issued in PCT/JP2019/010012, dated Jun. 4, 2019, pp. 1-6.
Uchibori et al., Brigatinib combined with anti-EGFR antibody overcomes osimertinib resistance in EGFR-mutated non-small-cell lung cancer, Nature Communications, Mar. 13, 2017, 8:14768, pp. 1-16.
European Patent Office, Extended European Search Report issued in EP Patent Application No. 19767893.1, dated Nov. 3, 2021, pp. 1-9.
Suzuki et al., "Development of a Novel, Fully-Automated Genotyping System: Principle and Applications", Sensors, Jan. 1, 2021, pp. 16614-16627, vol. 12(12).
Noriko et al., "Most T790M mutations are present on the same EGFR allele as activating mutations in patients with non-small cell lung cancer", Lung Cancer, Mar. 1, 2017, pp. 75-82, vol. 108.
Pont-Kingdon et al., "Direct molecular haplotyping by melting curve analysis of hybridization probes: beta 2-adrenergic receptor haplotypes as an example", Nucleic Acids Research, Jan. 1, 2005, pp. e89-l89, vol. 33 (10).

(Continued)

*Primary Examiner* — Narayan K Bhat
(74) *Attorney, Agent, or Firm* — PILLSBURY WINTHROP SHAW PITTMAN LLP

(57) ABSTRACT

A probe comprising a reporter region for detecting a first single nucleotide polymorphism, an anchor region for detecting a second single nucleotide polymorphism, and a linker region is disclosed. The reporter region comprises an oligonucleotide consisting of a sequence perfectly matching with the first target sequence, and a fluorescent dye that quenches when hybridized to the first target sequence where the first single nucleotide polymorphism is present. The anchor region comprises an oligonucleotide consisting of a sequence perfectly matching with a second target sequence where the second single nucleotide polymorphism is present. A length of the oligonucleotide of the reporter region is shorter than a length of the oligonucleotide of the anchor region.

16 Claims, 5 Drawing Sheets

Specification includes a Sequence Listing.

(56) References Cited

OTHER PUBLICATIONS

Lyon et al., "LightCycler Technology in Molecular Diagnostics", The Journal of Molecular Diagnostics, American Society for Investigative Pathology and the Association for Molecular Pathology, Mar. 1, 2009, pp. 93-101, vol. 11(2).

* cited by examiner

SEQUENCE LISTING

```
<160> NUMBER OF SEQ ID NOS: 19

<210> SEQ ID NO 1
<211> LENGTH: 16
<212> TYPE: DNA
<213> ORGANISM: Artificial Sequence
<220> FEATURE:
<223> OTHER INFORMATION: Synthetic

<400> SEQUENCE: 1
gctcatcatg cagctc                                                      16

<210> SEQ ID NO 2
```

```
<211> LENGTH: 19
<212> TYPE: DNA
<213> ORGANISM: Artificial Sequence
<220> FEATURE:
<223> OTHER INFORMATION: Synthetic

<400> SEQUENCE: 2
agctcatcac gcagctcat                                                  19

<210> SEQ ID NO 3
<211> LENGTH: 26
<212> TYPE: DNA
<213> ORGANISM: Artificial Sequence
<220> FEATURE:
<223> OTHER INFORMATION: Synthetic

<400> SEQUENCE: 3
catcatgcag ctcaaaaaaa acagcc                                          26

<210> SEQ ID NO 4
<211> LENGTH: 19
<212> TYPE: DNA
<213> ORGANISM: Artificial Sequence
<220> FEATURE:
<223> OTHER INFORMATION: Synthetic

<400> SEQUENCE: 4
agctcatcac gcagctcat                                                  19

<210> SEQ ID NO 5
<211> LENGTH: 12
<212> TYPE: DNA
<213> ORGANISM: Artificial Sequence
<220> FEATURE:
<223> OTHER INFORMATION: Synthetic

<400> SEQUENCE: 5
ttcggcagcc tc                                                         12

<210> SEQ ID NO 6
<211> LENGTH: 14
<212> TYPE: DNA
<213> ORGANISM: Artificial Sequence
<220> FEATURE:
<223> OTHER INFORMATION: Synthetic

<400> SEQUENCE: 6
ccttcggctg cctc                                                       14

<210> SEQ ID NO 7
<211> LENGTH: 18
<212> TYPE: DNA
<213> ORGANISM: Artificial Sequence
<220> FEATURE:
<223> OTHER INFORMATION: Synthetic

<400> SEQUENCE: 7
tggaaggggt ccatgtgc                                                   18

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
```
gggagccaat attgtctttg t                                            21

<210> SEQ ID NO 9
<211> LENGTH: 38
<212> TYPE: DNA
<213> ORGANISM: Artificial Sequence
<220> FEATURE:
<223> OTHER INFORMATION: Synthetic

<400> SEQUENCE: 9
cacgtaggct tcctggaggg tctggccacc atgcgaag                          38

<210> SEQ ID NO 10
<211> LENGTH: 38
<212> TYPE: DNA
<213> ORGANISM: Artificial Sequence
<220> FEATURE:
<223> OTHER INFORMATION: Synthetic

<400> SEQUENCE: 10
ggcatctgcc tcacctccac gttcccggac atagtcca                          38

<210> SEQ ID NO 11
<211> LENGTH: 17
<212> TYPE: DNA
<213> ORGANISM: Artificial Sequence
<220> FEATURE:
<223> OTHER INFORMATION: Synthetic

<400> SEQUENCE: 11
gaggcacgtc agtgtgg                                                 17

<210> SEQ ID NO 12
<211> LENGTH: 34
<212> TYPE: DNA
<213> ORGANISM: Artificial Sequence
<220> FEATURE:
<223> OTHER INFORMATION: Synthetic

<400> SEQUENCE: 12
cagctcatca tgcagctcat gcccttcggc agcc                              34

<210> SEQ ID NO 13
<211> LENGTH: 34
<212> TYPE: DNA
<213> ORGANISM: Artificial Sequence
<220> FEATURE:
<223> OTHER INFORMATION: Synthetic

<400> SEQUENCE: 13
cagctcatca tgcagctcat gcccttcggc tgcc                              34

<210> SEQ ID NO 14
<211> LENGTH: 34
<212> TYPE: DNA
<213> ORGANISM: Artificial Sequence
<220> FEATURE:
<223> OTHER INFORMATION: Synthetic

<400> SEQUENCE: 14
cagctcatca cgcagctcat gcccttcggc agcc                              34

<210> SEQ ID NO 15
<211> LENGTH: 12
<212> TYPE: DNA

```
<213> ORGANISM: Artificial Sequence
<220> FEATURE:
<223> OTHER INFORMATION: Synthetic

<400> SEQUENCE: 15
atcargcagc tc                                                              12

<210> SEQ ID NO 16
<211> LENGTH: 28
<212> TYPE: DNA
<213> ORGANISM: Homo sapiens

<400> SEQUENCE: 16
tagtacgtcg agtacgggaa gccgtcgg                                             28

<210> SEQ ID NO 17
<211> LENGTH: 28
<212> TYPE: DNA
<213> ORGANISM: Homo sapiens

<400> SEQUENCE: 17
tagtacgtcg agtacgggaa gccgacgg                                             28

<210> SEQ ID NO 18
<211> LENGTH: 28
<212> TYPE: DNA
<213> ORGANISM: Homo sapiens

<400> SEQUENCE: 18
tagtgcgtcg agtacgggaa gccgtcgg                                             28

<210> SEQ ID NO 19
<211> LENGTH: 19
<212> TYPE: DNA
<213> ORGANISM: Artificial Sequence
<220> FEATURE:
<223> OTHER INFORMATION: Synthetic

<400> SEQUENCE: 19
gtcgagtagt acgtcgagt                                                       19
```

OLIGONUCLEOTIDE PROBE FOR DETECTING SINGLE NUCLEOTIDE POLYMORPHISMS, AND METHOD FOR DETERMINING CIS-TRANS CONFIGURATION

RELATED PATENT APPLICATIONS

This patent application is a national phase filing of, and claims the benefit of, International Patent Application No. PCT/JP2019/010012, filed on Mar. 12, 2019, which claims priority to Japanese Patent Application No. 2018-047582, filed on Mar. 15, 2018, the contents of which are hereby incorporated by reference in their entirety.

SEQUENCE LISTING

The present application is being filed with a Sequence Listing. The Sequence Listing is submitted electronically in ASCII format via EFS-Web in the form of a text file. Said ASCII copy, created on Sep. 11, 2020, is named "Soei-0514280-Sequence Listing" and is 3.18 KB in size, the contents of which are incorporated herein by reference in their entirety.

TECHNICAL FIELD

The present invention relates to an oligonucleotide probe for detecting a single nucleotide polymorphism, and a method for determining whether two single nucleotide polymorphisms are present in the cis configuration or in the trans configuration.

BACKGROUND ART

Epidermal growth factor receptor (EGFR) is a transmembrane receptor tyrosine kinase, and is known as a factor involved in control of proliferation and growth of cells. EGFR is overexpressed as an oncogene in many cancers including lung cancer, and hence is regarded as a molecular target for cancer treatment, and drugs for cancer treatment such as an EGFR tyrosine kinase inhibitor (EGFR-TKI) have been developed.

It is, however, known that EGFR tyrosine kinase inhibitors such as gefitinib, erlotinib and afatinib develop resistance in about 1 year to cause re-exacerbation. It is a mutation (T790M) caused by replacement of threonine (T) corresponding to the 790th amino acid of EGFR by methionine (M), that occupies almost a half of the cause of the resistance development. Therefore, a probe capable of detecting T790M has been developed, and a probe for polymorphism detection designed to hybridize to a sequence of EGFR gene comprising T790M has been reported (Patent Literature 1 and Patent Literature 2). Besides, osimertinib, that is, an EGFR tyrosine kinase inhibitor effective against T790M, has been developed and used as a drug for lung cancer treatment.

It is, however, reported that the effects of all the clinically applied EGFR tyrosine kinase inhibitors are lost due to further addition of resistance mutations. One cause of this resistance is a mutation (C797S) caused by replacement of cysteine (C) corresponding to the 797th amino acid of EGFR by serine (S). It has been found that when the C797S is present in the trans configuration with respect to the T790M, a combination of existing EGFR-TKIs may be effective, but it has been reported that when the C797S is present in the cis configuration with respect to the T790M, the effects of all the clinically applied EGFR tyrosine kinase inhibitors including the combination are lost (Non Patent Literature 1). When the intensity of the resistance to a therapeutic agent or the like is varied in this manner depending on different positional relationship of the cis configuration and the trans configuration between different two single nucleotide polymorphisms (hereinafter sometimes abbreviated as "SNP") corresponding to a cause of the resistance to the therapeutic agent, a method for determining whether they are in the cis configuration or in the trans configuration is significant for, for example, selecting a countermeasure against the resistance and developing a therapeutic agent/method for overcoming the resistance. In a current situation, merely a complicated method using a next generation sequencer or digital PCR can be employed for determining whether they are in the cis configuration or in the trans configuration. Therefore, a probe for polymorphism detection for simply determining whether they are in the cis configuration or in the trans configuration is desired to be developed.

It is preferable that the probe for polymorphism detection is simply and inexpensively synthesized and can detect the presence of a polymorphism with accuracy and sensitivity. As such a probe, an oligonucleotide probe for single nucleotide polymorphism detection that comprises a reporter region for detecting a single nucleotide polymorphism, an anchor region that binds to a target sequence regardless of the presence/absence of a single nucleotide polymorphism, and a linker region linking the reporter region and the anchor region, and can detect the presence/absence of a single nucleotide polymorphism using a fluorescent dye comprised in the reporter region on the basis of fluorescence intensity thereof has been developed (Patent Literature 3).

CITATION LIST

Patent Literature

Patent Literature 1: International Publication No. WO2006/086777
Patent Literature 2: International Publication No. WO2011/052754
Patent Literature 3: International Publication No. WO2016/098595

Non Patent Literature

Non Patent Literature 1: K. Uchibori et al., Brigatinib combined with anti-EGFR antibody overcomes osimertinib resistance in EGFR-mutated non-small-cell lung cancer, Nature communications 8, Article number: 14768 (2017)

SUMMARY OF INVENTION

Technical Problem

An object of the present invention is to provide an oligonucleotide probe for single nucleotide polymorphism detection, for determining, in a target nucleic acid where a first single nucleotide polymorphism and a second single nucleotide polymorphism are present in different positions, whether the first single nucleotide polymorphism and the second single nucleotide polymorphism are present in the cis configuration or in the trans configuration. Another object of the present invention is to provide a method, using the oligonucleotide probe, for determining whether the first single nucleotide polymorphism and the second single nucleotide polymorphism are present in the cis configuration or in the trans configuration.

Solution to Problem

The present invention provides an oligonucleotide probe for single nucleotide polymorphism detection, for determining, in a target nucleic acid where a first single nucleotide polymorphism and a second single nucleotide polymorphism are present in different positions, whether the first single nucleotide polymorphism and the second single nucleotide polymorphism are present in a cis configuration or in a trans configuration, wherein the target nucleic acid comprises a first target sequence where the first single nucleotide polymorphism is present, and a second target sequence where the second single nucleotide polymorphism is present, the probe comprises a reporter region for detecting the first single nucleotide polymorphism, an anchor region for detecting the second single nucleotide polymorphism, and a linker region, the reporter region comprises an oligonucleotide consisting of a sequence perfectly matching with the first target sequence, and a fluorescent dye that quenches when the first target sequence and the reporter region hybridize, the anchor region comprises an oligonucleotide consisting of a sequence perfectly matching with the second target sequence, the linker region links the reporter region and the anchor region, and comprises an oligonucleotide consisting of a sequence non-complementary to a sequence disposed between the first target sequence and the second target sequence in the target nucleic acid when the first single nucleotide polymorphism and the second single nucleotide polymorphism are present in the cis configuration, and a length of the oligonucleotide of the reporter region is shorter than a length of the oligonucleotide of the anchor region.

The probe of the present invention comprises, separately from the reporter region for detecting the first single nucleotide polymorphism, the anchor region for detecting the second single nucleotide polymorphism, and these regions are linked by the linker region. Besides, the length of the oligonucleotide of the reporter region is shorter than the length of the oligonucleotide of the anchor region. Therefore, if the binding property of the probe is attained by hybridization of the anchor region to the second target sequence, the presence/absence of the first single nucleotide polymorphism can be sensitively detected by the reporter region linked by the linker region and comprising the fluorescent dye. If appropriate adjustment is performed so that the fluorescence intensity can be reduced when both the reporter region and the anchor region hybridize respectively to the corresponding target sequences, it can be determined whether the first single nucleotide polymorphism and the second single nucleotide polymorphism are present in the cis configuration or in the trans configuration with good accuracy and detection sensitivity, by using a single probe.

The linker region is preferably an oligonucleotide consisting of a sequence comprising no universal base. If a universal base is not used in the linker region, the probe can be more inexpensively synthesized.

The linker region is preferably an oligonucleotide consisting of only one kind of base selected from adenine, guanine, cytosine or thymine. Thus, the possibility of causing the linker region of the probe to bind to the target nucleic acid is lowered, and hence, the flexibility of the reporter region is increased, and the detectability for the first single nucleotide polymorphism and the second single nucleotide polymorphism can be improved. Besides, if the linker region consists of the above-described base alone, the probe can be more inexpensively synthesized.

The linker region is preferably an oligonucleotide consisting of 3 to 11 nucleotides. Thus, the anchor region and the reporter region are spaced from each other by a prescribed distance, and hence, the flexibility of the reporter region is increased and the detectability for the first single nucleotide polymorphism can be improved, resulting in improving the detectability for SNPs in the cis configuration.

The present invention also provides a method for determining whether a first single nucleotide polymorphism and a second single nucleotide polymorphism are present in a cis configuration or in a trans configuration, comprising: preparing a mixture by mixing the above-described probe of the present invention, and a target nucleic acid where the first single nucleotide polymorphism and the second single nucleotide polymorphism are present in different positions; measuring fluorescence intensity of the mixture; and determining, on the basis of the fluorescence intensity, whether the first single nucleotide polymorphism and the second single nucleotide polymorphism are present in the cis configuration or in the trans configuration.

According to the method of the present invention, it can be determined whether a first single nucleotide polymorphism and a second single nucleotide polymorphism are present in the cis configuration or in the trans configuration, by using a single probe, on the basis of the fluorescence intensity.

Advantageous Effects of Invention

According to the present invention, it can be simply determined, by using a single probe and without requiring a complicated step, whether a first single nucleotide polymorphism and a second single nucleotide polymorphism are present in the cis configuration or in the trans configuration in a target nucleic acid where the first single nucleotide polymorphism and the second single nucleotide polymorphism are present in different positions.

DESCRIPTION OF EMBODIMENTS

Figure 1:
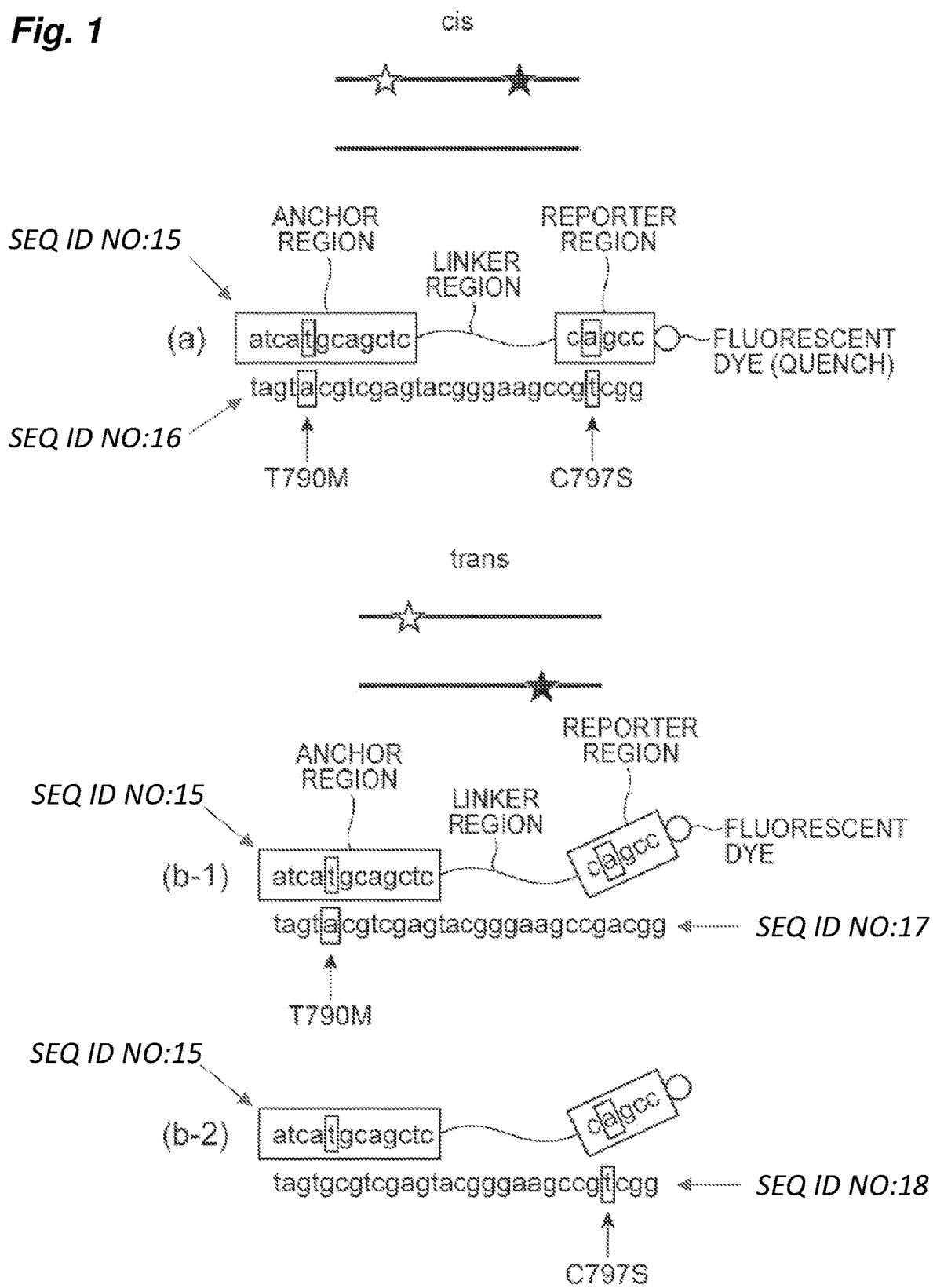
FIG. 1 is a schematic diagram of a mechanism for detecting, by using a probe of an embodiment of the present invention, T790M and C797S present in the cis configuration. Each boxed portion indicates an SNP or a portion corresponding to an SNP.

Embodiments of the present invention (hereinafter referred to as the "present embodiment") will now be described in detail. It is noted that the present invention is not limited to the following embodiments.

Herein, the term "single nucleotide polymorphism (SNP)" refers to a polymorphism caused by replacement of one base in a sequence.

Herein, the term "target nucleic acid" refers to a nucleic acid to be checked for the presence/absence of an SNP by using a probe of the present embodiment. The target nucleic acid comprises a first target sequence that is a region where a first single nucleotide polymorphism is present, and a second target sequence that is a region where a second single nucleotide polymorphism is present. The first target sequence and the second target sequence can be determined beforehand based on a sequence of a nucleic acid in which an SNP is known to be present.

The first single nucleotide polymorphism and the second single nucleotide polymorphism are present in a positional relationship of either the cis configuration or the trans configuration. The cis configuration means that the first single nucleotide polymorphism and the second single nucleotide polymorphism are positioned on the same chromosome, and the trans configuration means that the first single nucleotide polymorphism and the second single nucleotide polymorphism are positioned on different chromosomes. When the first single nucleotide polymorphism and the second single nucleotide polymorphism can be present on the same allele, the cis configuration means that the first single nucleotide polymorphism and the second single nucleotide polymorphism are positioned on the same allele, and the trans configuration means that the first single nucleotide polymorphism and the second single nucleotide polymorphism are positioned on different alleles. An example of the case where the first single nucleotide polymorphism and the second single nucleotide polymorphism can be present on the same allele includes an EGFR gene, in which the first single nucleotide polymorphism can be C797S and the second single nucleotide polymorphism can be T790M.

The first target sequence is preferably a region comprised in the sequence of the nucleic acid in which an SNP is known to be present, and consisting of 3 to 6 nucleotides including a base where the SNP desired to be detected (the first single nucleotide polymorphism) can occur. The first target sequence is more preferably a region consisting of 3 to 5 nucleotides, and further preferably a region consisting of 4 or 5 nucleotides. A position of the base where the SNP can occur in the first target sequence is not especially limited, and is preferably in the vicinity of the center of the first target sequence.

The second target sequence is preferably a region not overlapping the first target sequence, comprised in the sequence of the nucleic acid in which an SNP is known to be present, and consisting of 8 to 20 nucleotides including a base where the SNP desired to be detected (the second single nucleotide polymorphism) can occur. The second target sequence is more preferably a region consisting of 10 to 18 nucleotides, further preferably a region consisting of 11 to 15 nucleotides, and particularly preferably a region consisting of 14 or 15 nucleotides. A position of the base where the SNP can occur in the second target sequence is not especially limited, and is preferably in the vicinity of the center of the second target sequence.

When the first single nucleotide polymorphism and the second single nucleotide polymorphism are present in the positional relationship of the cis configuration, the second target sequence is positioned on the 3' or 5' side of the first target sequence. When the second target sequence is positioned on the 3' side of the first target sequence, the number of nucleotides disposed between the 3'-end of the first target sequence and the 5'-end of the second target sequence (an interval) is preferably 0 to 15, more preferably 3 to 12, and further preferably 4 to 10. If the distance between the first target sequence and the second target sequence is set to fall in the above-described range, an appropriate distance can be retained between a reporter region and an anchor region of a probe according to the present embodiment, and therefore, the SNP detectability tends to be improved. Besides, since the length of a linker region can be set in accordance with the distance between the first target sequence and the second target sequence, there is no need to synthesize an unnecessary nucleotide, and hence it also tends to be economically advantaged. If the second target sequence is positioned on the 5' side of the first target sequence, the number of nucleotides disposed between the 5'-end of the first target sequence and the 3'-end of the second target sequence can be set to fall in the above-described range.

Examples of the target nucleic acid of the present embodiment include a DNA and an RNA, and it is preferably a DNA. The origin of the target nucleic acid is not especially limited as long as a DNA or an RNA is comprised, and examples include animals, plants, fungi, microorganisms and viruses. Besides, a preparation method for the target nucleic acid is also not especially limited, and it may be prepared directly from an organism or a virus, may be prepared from a specific tissue, may be prepared by artificial cloning from a nucleic acid used as a template, or may be prepared by using an amplification product obtained by a PCR method or a LAMP method.

Herein, the term "perfect match" means that a sequence of a reporter region is completely complementary to the first target sequence of the target nucleic acid and hence the first target sequence and the reporter region hybridize. On the contrary, the term "mismatch" means that the sequence of the reporter region is different, even in one base, from the sequence of the target nucleic acid and hence the sequence and the reporter region are difficult to hybridize as compared with the case of the perfect match.

<Probe>

The probe of the present embodiment comprises the reporter region for detecting the first single nucleotide polymorphism, the anchor region for detecting the second single nucleotide polymorphism, and the linker region. In the probe of the present embodiment, the positional relationship between the reporter region and the anchor region can be appropriately set in accordance with the positional relationship between the first target sequence and the second target sequence when the first single nucleotide polymorphism and the second single nucleotide polymorphism are present in the positional relationship of the cis configuration in the target nucleic acid. For example, if the second target sequence is positioned on the 3' side of the first target sequence, the anchor region is disposed on the 5' side of the reporter region.

The probe of the present embodiment comprises, separately from the reporter region for detecting the first single nucleotide polymorphism, the anchor region that binds to the target sequence for detecting the second single nucleotide polymorphism. The length of the oligonucleotide of the reporter region is shorter than the length of the oligonucleotide of the anchor region. Therefore, if the binding property of the probe is attained by hybridizing the anchor region to the second target sequence, the presence/absence of the first single nucleotide polymorphism can be more accurately and sensitively detected by the reporter region linked by the linker region.

A method for producing the probe of the present embodiment is not especially limited, and an example includes a usual oligonucleotide synthesis method employing chemical synthesis. The probe of the present embodiment is constituted by a usual oligonucleotide and hence can be simply and inexpensively produced without employing a complicated synthesis method.

(Reporter Region)

The reporter region is a region for detecting the first single nucleotide polymorphism. An oligonucleotide of the reporter region is a nucleotide consisting of a sequence complementary to the first target sequence where the first single nucleotide polymorphism is present. The reporter region is an oligonucleotide consisting of a sequence perfectly matching with the first target sequence where the first single nucleotide polymorphism is present, and mismatching with a sequence other than the first target sequence (including a sequence identical to the first target sequence except that the first single nucleotide polymorphism is not present).

Besides, the reporter region comprises a fluorescent dye that quenches when the first target sequence and the reporter region hybridize. Since the reporter region comprises such a fluorescent dye, the single nucleotide polymorphism can be simply detected by measuring the fluorescence intensity. Examples of the fluorescent dye having such a characteristic include QProbe series (manufactured by Nippon Steel & Sumikin Eco-Tech Corporation). If guanine is present in the vicinity of a base complementary to a base modified with the fluorescent dye when the probe hybridizes, fluorescence resonance energy transfer occurs and hence the fluorescence quenches in the QProbe. Specific examples of the fluorescent dye comprised in the QProbe include Pacific Blue, ATTO465, BODIPY-FL, Rhodamine 6G, TAMRA and ATTO655. When such a fluorescent dye is used, the fluorescent characteristic varies depending on whether or not the reporter region and the first target sequence hybridize. Therefore, the probe of the present embodiment is economically excellent because there is no need to add a quencher as in a usual SNP detection method using a probe comprising a fluorescent dye. The fluorescent dye is preferably bound to an end of the reporter region opposite to the linker region.

From the viewpoint of further improving the single nucleotide polymorphism detectability, the length of the oligonucleotide of the reporter region is preferably 3 to 6 nucleotides, more preferably 3 to 5 nucleotides, and further preferably 4 or 5 nucleotides. Besides, from the viewpoint of improving the detectability for SNPs in the cis configuration, the length of the oligonucleotide of the reporter region is preferably shorter than the length of an oligonucleotide of the anchor region in the probe of the present embodiment. From the viewpoint that the reporter region hybridizes to the target nucleic acid for quenching the fluorescence of the fluorescent dye, the oligonucleotide of the reporter region is preferably designed so that guanine is present in the first target sequence within 1 to 3 bases from the binding portion of the fluorescent dye.

(Anchor Region)

The anchor region is a region for detecting the second single nucleotide polymorphism. An oligonucleotide of the anchor region is a nucleotide consisting of a sequence complementary to the second target sequence where the second single nucleotide polymorphism is present. The anchor region is an oligonucleotide consisting of a sequence perfectly matching with the second target sequence where the second single nucleotide polymorphism is present, and mismatching with a sequence other than the second target sequence (including a sequence identical to the second target sequence except that the second single nucleotide polymorphism is not present). From the viewpoint of attaining good binding property to the second target sequence, the length of the oligonucleotide of the anchor region is preferably 8 to 20 nucleotides, more preferably 10 to 18 nucleotides, further preferably 11 to 15 nucleotides, and particularly preferably 14 or 15 nucleotides.

(Linker Region)

The linker region is a region for increasing the flexibility of the probe. The linker region links the reporter region and the anchor region. The linker region has an oligonucleotide consisting of a sequence non-complementary to a sequence disposed between the first target sequence and the second target sequence in the target nucleic acid when the first single nucleotide polymorphism and the second single nucleotide polymorphism are present in the cis configuration.

From the viewpoint that the probe can be more inexpensively synthesized, the linker region preferably comprises no universal base. Examples of the universal base include universal bases that are bases other than adenine, guanine, cytosine, thymine and uracil, and analogs thereof. Examples of the universal bases and the analogs thereof include 5-nitroindole, deoxyriboside, 3-nitropyrrole deoxyriboside, 4-nitrobenzimidazole deoxyriboside, deoxynebularine, deoxyinosine, 2'-OMe inosine, 2'-OMe 5-nitroindole riboside, 2'-OMe 3-nitropyrrole riboside, 2'-F inosine riboside, 2'-F nebularine, 2'-F 5-nitroindole riboside, 2'-F 4-nitrobenzimidazole riboside, 2'-F 3-nitropyrrole riboside, PNA-5-nitroindole (introindole), PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'-O-methoxyethyl nebularine, 2'-O-methoxyethyl 5-nitroindole riboside, 2'-O-methoxyethyl 4-nitro-benzimidazole riboside, 2'-O-methoxyethyl 3-nitropyrrole riboside, and deoxy $R_pMP$-5-nitroindole dimer 2'-OMe $R_pMP$-5-nifroindole dimer.

The linker region is preferably an oligonucleotide consisting of only one kind of base selected from adenine, guanine, cytosine and thymine. Thus, the possibility of causing the linker region to bind to the target nucleic acid is lowered, and hence, the flexibility of the reporter region is increased, and the detectability for SNPs in the cis configuration can be easily improved. Besides, if the linker region consists of the above-described base alone, there is a tendency that the probe can be more inexpensively synthesized.

Besides, the length of the oligonucleotide of the linker region is preferably 3 to 11 nucleotides, more preferably 3 to 9 nucleotides, and particularly preferably 7 nucleotides. If the length of the oligonucleotide of the linker region falls in the above-described range, the anchor region that binds to the target nucleic acid is spaced by a prescribed distance from the reporter region, and hence, the flexibility of the reporter region is increased and the detectability for SNPs in the cis configuration tends to be improved. Besides, from the viewpoint of attaining the flexibility in the conformational structure in hybridization of the target nucleic acid and the probe of the present embodiment, the length of the oligonucleotide of the linker region is preferably −5 to +5 nucleotides, and more preferably −3 to +3 nucleotides as compared with the distance (the interval) between the first target sequence and the second target sequence.

<Method, Using Probe, for Determining Whether First Single Nucleotide Polymorphism and Second Single Nucleotide Polymorphism are Present in Cis Configuration or Trans Configuration>

Since the probe of the present embodiment comprises the fluorescent dye in the reporter region for detecting the first single nucleotide polymorphism, the presence/absence of the first single nucleotide polymorphism in the target nucleic acid can be detected on the basis of the fluorescence intensity.

An embodiment of the method for determining whether the first single nucleotide polymorphism and the second single nucleotide polymorphism are present in the cis configuration or in the trans configuration is, for example, a method including preparing a mixture by mixing the probe of the present embodiment and a target nucleic acid where a first single nucleotide polymorphism and a second single nucleotide polymorphism are present in different positions, measuring fluorescence intensity of the mixture, and determining, on the basis of the measured fluorescence intensity, whether the first single nucleotide polymorphism and the second single nucleotide polymorphism are present in the cis configuration or in the trans configuration.

FIG. 1 is a diagram schematically illustrating a state obtained by mixing the probe of the present embodiment and a target nucleic acid when the first single nucleotide polymorphism is C797S and the second single nucleotide polymorphism is T790M. In the anchor region having a sequence complementary to a second target sequence where T790M is present, the probe hybridizes to the target nucleic acid (FIGS. 1(a) and (b-1)). Then, when the reporter region hybridizes to a first target sequence where C797S is present, the fluorescence of the fluorescent dye quenches (FIG. 1(a)). In this case, it can be determined that C797S and T790M are present in the cis configuration. On the other hand, in the case where the reporter region mismatches, the reporter region cannot hybridize, and hence the fluorescence of the fluorescent dye is continuously emitted (FIG. 1(b-1)). In this case, it can be determined that C797S and T790M are present in the trans configuration. Besides, in the probe of the present embodiment, the length of the nucleotide of the reporter region is shorter than the length of the nucleotide of the anchor region, and hence the binding property of the probe is attained owing to the anchor region. Therefore, in the case where the anchor region mismatches, the reporter region cannot hybridize to the first target sequence even if C797S is present in the first target sequence, and the fluorescence of the fluorescent dye is continuously emitted (FIG. 1(b-2)). Also in this case, it can be determined that C797S and T790M are present in the trans configuration.

The probe of the present embodiment emits the fluorescence if the reporter region does not hybridize to the first target sequence in the target nucleic acid. Accordingly, for example, if the fluorescence intensity of the mixture obtained by mixing the probe and the target nucleic acid is reduced as compared with that before mixing, it can be determined that the first single nucleotide polymorphism and the second single nucleotide polymorphism are present in the cis configuration. On the contrary, if the fluorescence intensity of the mixture obtained by mixing the probe and the target nucleic acid is retained or increased as compared with that before mixing, it can be determined that the first single nucleotide polymorphism and the second single nucleotide polymorphism are present in the trans configuration. Since the fluorescence intensity can be also measured at room temperature (about 25° C.), it can be efficiently determined by the method of the present embodiment whether the first single nucleotide polymorphism and the second single nucleotide polymorphism are present in the cis configuration or in the trans configuration.

Another embodiment of the method for SNP detection is, for example, a method of performing Tm (Melting Temperature) analysis. The Tm analysis can be performed by a method usually employed by those skilled in the art. The Tm analysis can be performed, for example, by a method in which the probe and the target nucleic acid are mixed, and the fluorescence intensity of a mixture thus obtained is measured while changing the temperature of the mixture. If the reporter region mismatches, the thermal stability of a complex of the probe and the target nucleic acid is lower than in the case of perfect match, and hence, the reporter region binds to the target nucleic acid and the fluorescence quenching is observed at a lower temperature. The temperature at this time is designated as a quenching start temperature. On the other hand, if the reporter region perfectly matches, the thermal stability of the complex of the probe and the target nucleic acid is higher than in the case of the mismatch, and hence, the reporter region binds to the target nucleic acid and the fluorescence quenching is observed even at a higher temperature. Accordingly, for example, the quenching start temperature of the target nucleic acid obtained when the reporter region mismatches is measured, and if a quenching start temperature is higher than this value, it can be determined that the first single nucleotide polymorphism and the second single nucleotide polymorphism are present in the cis configuration in the target nucleic acid used in the measurement. In a case where the specificity of the reporter region is so high that the fluorescence quenching is not measured at all in the case of the mismatch, however, for example, the quenching start temperature of the target nucleic acid obtained when the anchor region mismatches is measured, and if a quenching start temperature is higher than this value, it can be determined that the first single nucleotide polymorphism and the second single nucleotide polymorphism are present in the cis configuration in the target nucleic acid used in the measurement.

In the method, of the present embodiment, for determining whether the first single nucleotide polymorphism and the second single nucleotide polymorphism are present in the cis configuration or in the trans configuration, a competing oligonucleotide can be further mixed in the preparing a mixture by mixing the probe and a target nucleic acid where a first single nucleotide polymorphism and a second single nucleotide polymorphism are present in different positions. The competing oligonucleotide may be an oligonucleotide having a sequence completely complementary to a wild type sequence of the first target sequence, may be an oligonucleotide having a sequence completely complementary to a wild type sequence of the second target sequence, or may be a combination of these, and is preferably an oligonucleotide having a sequence completely complementary to the wild type sequence of the second target sequence. The detection accuracy for SNPs in the cis configuration can be improved by thus further adding a competing oligonucleotide.

Since the probe of the present embodiment hybridizes to the target nucleic acid in the anchor region through the second target sequence, the length of the nucleotide of the reporter region for detecting the first single nucleotide polymorphism can be made very short. Therefore, the specificity of the reporter region becomes high, and hence, the reporter region is difficult to hybridize to a mismatched sequence under a low temperature condition such as room temperature. As a result, in the case of the mismatch, the fluorescence intensity of the mixture at around room temperature is not conspicuously lowered as compared with the fluorescence intensity at the quenching start temperature. On the other hand, in the case where the reporter region perfectly matches, the reporter region hybridizes to the target nucleic acid through the first target sequence at around room temperature. Therefore, in the case of the perfect match, the fluorescence intensity of the mixture at around room temperature is conspicuously lowered as compared with the fluorescence intensity at the quenching start temperature, and is about 60% or less. Accordingly, in the SNP detection method employing the Tm analysis, for example, if the fluorescence intensity of the mixture at around room temperature is 60% or less as compared with the fluorescence intensity at the quenching start temperature, it can be determined that the first single nucleotide polymorphism and the second single nucleotide polymorphism are present in the cis configuration in the target nucleic acid used in the measurement.

In the determination method of the present embodiment, an amplification product amplified by the PCR method, the LAMP method or the like can be used as the target nucleic acid.

According to the probe and the determination method of the present embodiment, for example, for a patient having a disease changed in disease conditions because a first single nucleotide polymorphism and a second single nucleotide polymorphism are present in different positional relationships of the cis configuration and the trans configuration, an index for diagnosis or for selection of a proper therapeutic agent/method or the like can be provided. Alternatively, for example, for a patient having a disease changed in reaction to a therapeutic agent because a first single nucleotide polymorphism and a second single nucleotide polymorphism are present in different positional relationships of the cis configuration and the trans configuration, an index for selection of a proper therapeutic agent/method or the like can be provided. Alternatively, for example, in a case where the intensity of the resistance to a therapeutic agent or the like is varied because a first single nucleotide polymorphism and a second single nucleotide polymorphism, corresponding to a cause of the resistance to the therapeutic agent, are present in different positional relationships of the cis configuration or the trans configuration, an index for selection of a countermeasure against the resistance, and for development or the like of a therapeutic agent/method for overcoming the resistance can be provided.

EXAMPLES

The present invention will now be described more specifically with reference to Examples, and it is noted that the present invention is not limited to these Examples.

Example 1: Design of Probe and Primer for LAMP Method

As a reference sequence, a sequence of Homo sapiens epidermal growth factor receptor (EGFR), RefSeqGene (LRG_304) on chromosome 7 (NCBI accession No. NG_007726) was used. Mutations occurring in the EGFR gene are as follows:

TABLE 1

| Mutation | Exon | Nucleotide Mutation | Abbreviation |
|---|---|---|---|
| deletions | 19 | 2235_2249del15 | B |
| | | 2238_2248 > GC | E1 |
| | | 2238_2252 > GCA | E2 |
| | | 2239_2247del9 | E3 |
| | | 2239_2251 > C | E4 |
| | | 2238_2255del18 | E5 |
| | | 2239_2248 > C | E6 |
| | | 2235_2252 > AAT | E7 |
| | | 2236_2253del18 | E8 |
| | | 2236_2250del15 | E9 |
| | | 2237_2251del15 | E10 |
| | | 2237_2255 > T | E11 |
| | | 2237_2254del18 | E12 |
| | | 2239_2253del15 | E13 |
| | | 2239_2256del18 | E14 |
| | | 2239_2258 > CA | E15 |
| | | 2240_2251del12 | E16 |
| | | 2240_2254del15 | E17 |
| | | 2240_2257del18 | E18 |
| insertion | 20 | 2307_2308insGCCAGCGTG | E19 |
| | | 2319_2320insCAC | E20 |
| | | 2310_2311insGGT | E21 |
| G719A | 18 | 2156G > C | G719A |
| G719C | 18 | 2155G > T | G719C |
| G719S | 18 | 2155G > A | G719S |
| S768I | 20 | 2303G > T | S768I |
| T790M | 20 | 2369C > T | T790M |
| L858R | 21 | 2573T > G | L858R |

TABLE 1-continued

| Mutation | Exon | Nucleotide Mutation | Abbreviation |
|---|---|---|---|
| L861Q | 21 | 2582T > A | L861Q |
| C797S | 20 | 2389T > A | C797S_1 |
| C797S | 20 | 2390G > C | C797S_2 |

In this example, T790M and C797S were selected among these mutations. A probe and a competing oligonucleotide sequence for T790M detection, a probe and a competing oligonucleotide sequence for single detection of C797S, and a probe and a competing oligonucleotide sequence for detection of T790M and C797S present in the cis configuration were designed as shown in Table 2. It is known that two mutations of 2389T>A and 2390G>C occur in C797S, and a probe for C797S detection based on 2389T>A having a higher detection frequency was designed. Hereinafter, C797S caused by the mutation of 2389T>A is sometimes designated as C797S_1, and C797S caused by the mutation of 2390G>C is sometimes designated as C797S_2.

DNAs alone or a mixture of these DNAs are used as the template DNA.

QProbe Binding Probe: A probe obtained by binding a QProbe to a DNA having a sequence of SEQ ID NO: 5 (probe for C797S detection).

LAMP Primer: A primer having a sequence of any one of SEQ ID NOS: 7 to 10.

LAMP Master Mix: 30 mM KCl, 1.8% Dextran, 14 mM Tricine, 0.1% n-heptyl, 0.5% Tween, 0.3% FCP, 1 mM DTT, 1.7 mM each dNTPs, 8 mM MgSO$_4$, 1.6 µm Forward inner primer (FIP, SEQ ID NO: 9), Backward inner primer (BIP, SEQ ID NO: 10), 0.8 µM Loop primer (LP, SEQ ID NO: 11), 0.2 µM F3 (SEQ ID NO: 7), 0.2 µM B3 (SEQ ID NO: 8), 1.2 µM competing oligonucleotide, 0.04 µM probe, 0.0375× intercalator (gel green), 19.7 U Bst DNA polymerase (aforementioned concentrations being final concentrations in 25 µL).

(Method)

To 20 µl of the LAMP master mix, 5 µl of heat-denatured template DNA (amount of template: 10000 cps) was added to prepare a reaction solution. The reaction solution was

TABLE 2

| | | Probe | | | Competing Oligonucleotide | |
|---|---|---|---|---|---|---|
| Probe Name | Target Mutation | Sequence (5' to 3') | SEQ ID NO | QProbe | Sequence | SEQ ID NO |
| Probe for T790M Detection | T790M | GCTCATCA[T] GCAGCTC | 1 | TAMRA | AGCTCATCACGCAGCT CAT | 2 |
| Linker Probe for Cis Configuration Detection | C797S_1, T790M (cis configuration) | CATCA[T] GCAGCTCA[A AAAAAA]C[A] GCC | 3 | TAMRA BODIPY | AGCTCATCACGCAGCT CAT | 4 |
| Probe for C797S Detection | C797S_1 (2389T>A) | TTCGGC[A] GCCTC | 5 | TAMRA | CCTTCGGCTGCCTC | 6 |

An underlined portion indicates a BNA synthesized portion, a boxed portion indicates a portion corresponding to an SNP, I indicates inosine, and [ ] indicate a linker sequence. A QProbe is bound to an end of the reporter region opposite to the linker sequence.

A primer for the LAMP method was designed as follows:

TABLE 3

| Target Mutation | Primer Name | Sequence | SEQ ID NO |
|---|---|---|---|
| T790M, C797S | EGFR_T790M_3_ID2-F3 | TGGAAGGGGTCCATGTGC | 7 |
| | EGFR_T790M_3_ID2-B3 | GGGAGCCAATATTGTCTTTGT | 8 |
| | EGFR_T790M_3_ID2-FIP | CACGTAGGCTTCCTGGAGGGTCTGGCCACCATGCGAAG | 9 |
| | EGFR_T790M_3_ID2-BIP | GGCATCTGCCTCACCTCCACGTTCCCGGACATAGTCCA | 10 |
| | EGFR_T790M_3__ID2-LF1 | GAGGCACGTCAGTGTGG | 11 |

Example 2: Detection of C797S_1 by LAMP Method

C797S detectability of the probe (probe for C797S detection shown in Table 2) for single detection of C797S_1 (2389T>A) designed in Example 1 was measured by the LAMP method.

(Materials)

Template DNA: A DNA having an EGFR gene sequence comprising C797S_1 (2389T>A), a DNA having an EGFR gene sequence comprising C797S_2 (2390G>C), and a DNA having a wild type EGFR gene sequence. One of these incubated at 65° C. for 90 minutes in a real-time fluorophotometer LC480 (manufactured by Roche), an amplified product thus obtained was heat-denatured at 95° C. for 5 minutes, and the resultant amplified product and the QProbe binding probe were caused to hybridize at 37° C. for 5 minutes. After the reaction, the temperature of the resultant reaction solution was gradually increased (acquisition 7/° C.) from 37° C. to 80° C., and the fluorescence intensity was measured for performing the thermal melting curve analysis. The fluorescence intensity was measured at 465/510 (nm) when the QProbe contained Bodipy FL, and was measured at 533/580 (nm) when the QProbe contained TAMRA.

(Results)

Figure 2:
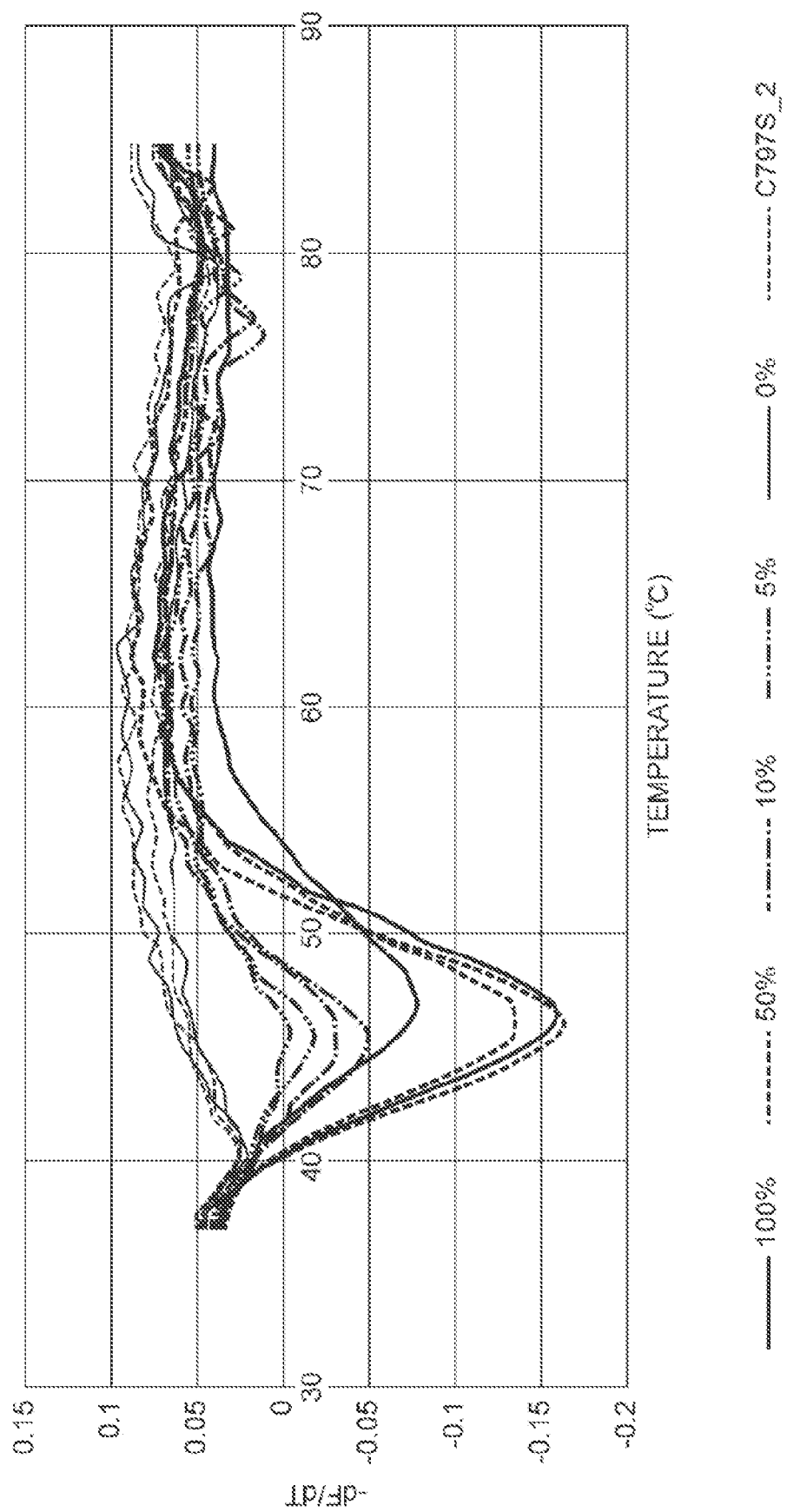
FIG. 2 illustrates results of thermal melting curve analysis obtained by using a probe for C797S detection. A curve of 100% corresponds to a case where all template DNAs are DNAs having an EGFR gene sequence comprising C797S_1, curves of 50% to 5% respectively correspond to cases where a ratio of DNAs having the EGFR gene sequence comprising C797S_1 in the template DNAs are respectively 50% to 5% (with the other DNAs being DNAs having a wild type EGFR gene sequence), a curve of 0% corresponds to a case where all the template DNAs are DNAs having the wild type EGFR gene sequence, and a curve of C797S_2 corresponds to a case where all the template DNAs are DNAs having an EGFR gene sequence comprising C797S_2.

The change of the fluorescence intensity during the thermal melting curve analysis is illustrated in FIG. 2. It was revealed that if the probe for C797S detection designed in Example 1 is used, a mutation content of C797S_1 up to 5% can be detected when the amount of the template is 10000 cps. Here, the term "mutation content" means a ratio of template DNAs comprising the mutation in the whole template DNAs.

Example 3: Screening of Cis Linker Probe by LAMP Method

Figure 3:
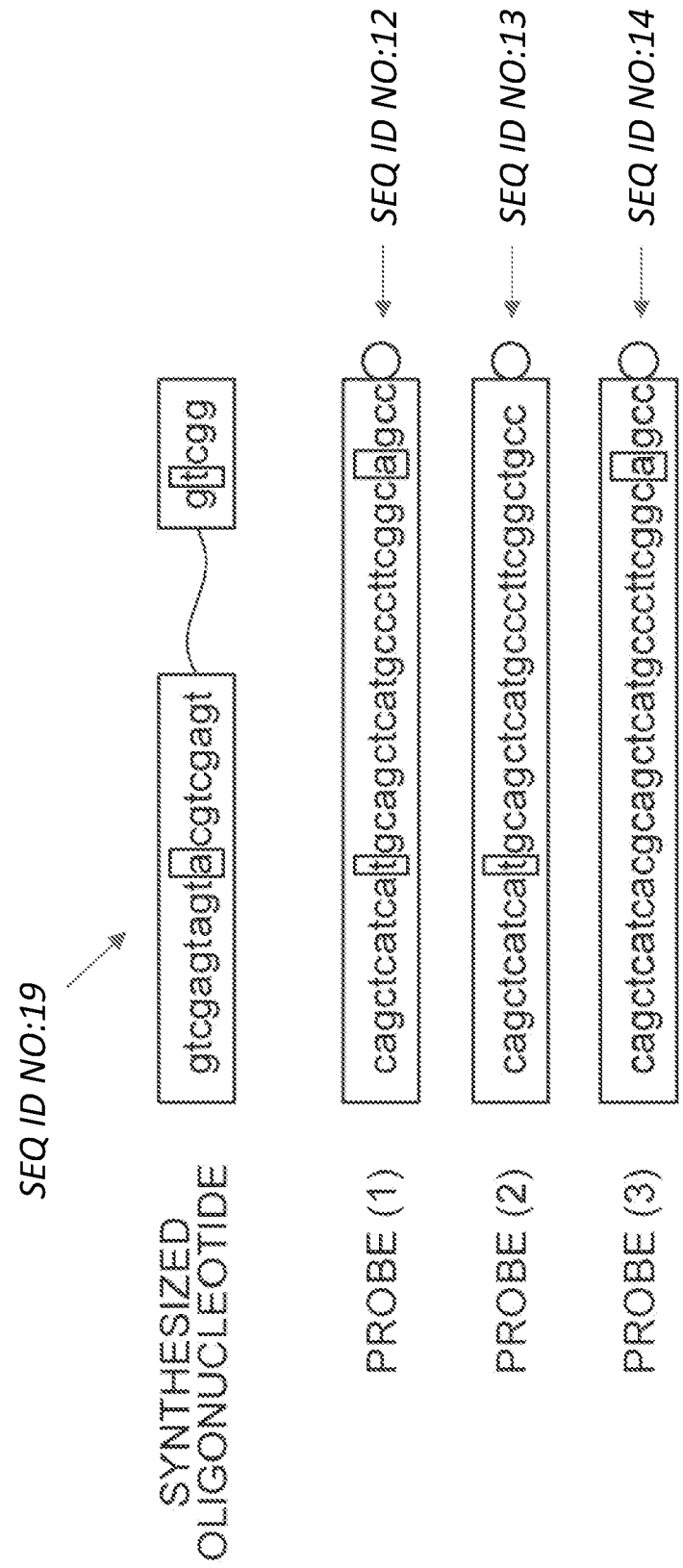
FIG. 3 is a schematic diagram of three probes (1) to (3) designed in Example 3, and a synthesized oligonucleotide in which a sequence that recognizes T790M and a sequence that recognizes C797S are bound to each other by a linker. Each boxed portion indicates an SNP or a portion corresponding to an SNP, and each circle bound to an end opposite to a linker region in each probe indicates a QProbe.

Three probes (1) to (3) having the same length were produced as illustrated in FIG. 3. The QProbe (TAMRA) was bound to each probe.
(1) Probe consisting of a sequence comprising T790M and C797S (SEQ ID NO: 12)
(2) Probe consisting of a sequence comprising T790M and a wild type sequence (SEQ ID NO: 13)
(3) Probe consisting of a wild type sequence and a sequence comprising C797S (SEQ ID NO: 14)

On the other hand, a synthesized oligonucleotide in which a sequence that recognizes T790M and a sequence that recognizes C797S were bound to each other by a linker was designed. Without changing the sequence that recognizes T790M, the lengths of the sequence that recognizes C797S and the linker were respectively changed to design four types of synthesized oligonucleotides as shown in Table 4.

TABLE 4

Synthesized Oligonucleotides Used in Screening

| No. | Length of C797S Recognition Sequence | Length of Linker |
| --- | --- | --- |
| C797S-1 | 5mer | 7mer |
| C797S-2 | 5mer | 9mer |
| C797S-3 | 4mer | 7mer |
| C797S-4 | 5mer | 5mer |

Figure 4:
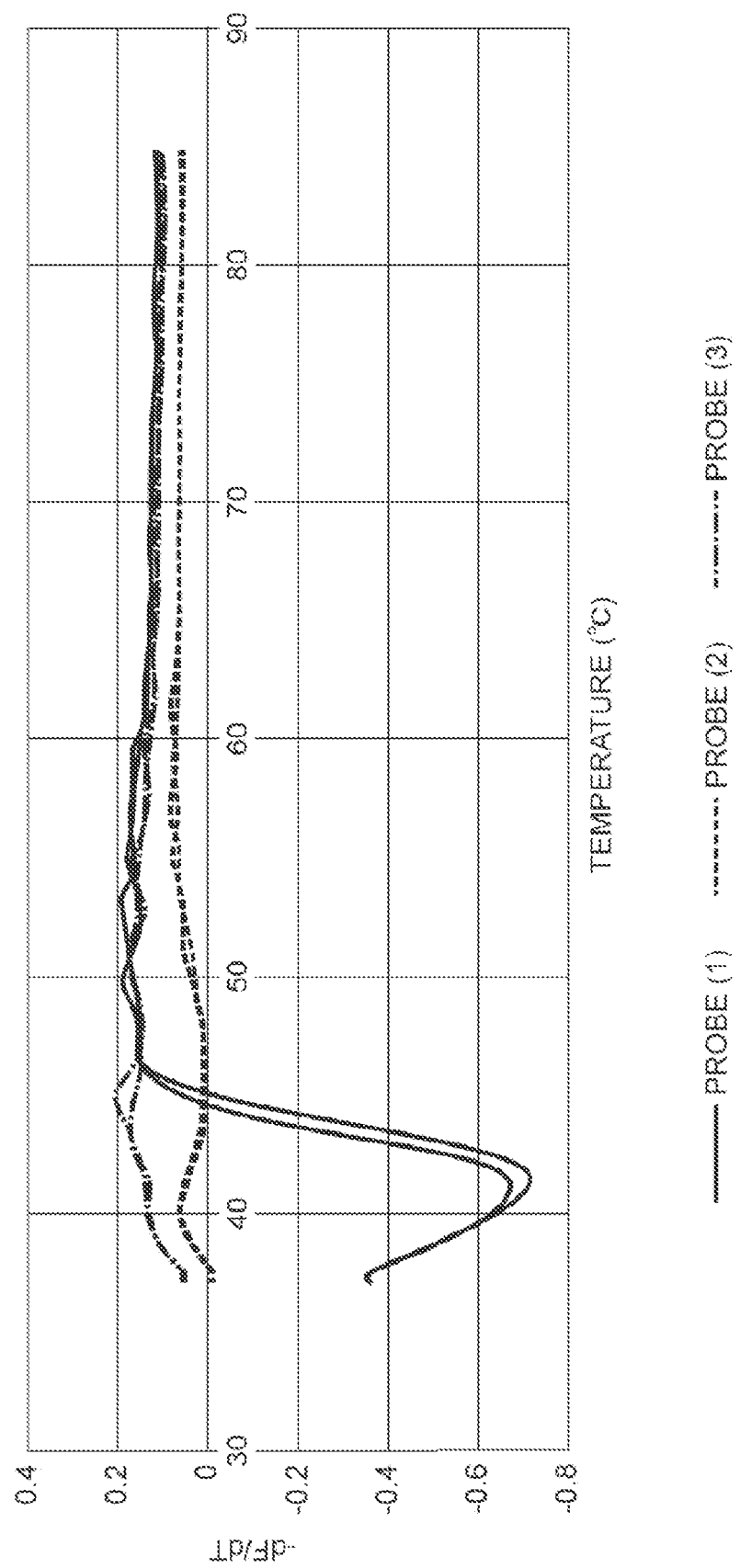
FIG. 4 illustrates results of thermal melting curve analysis obtained by using the synthesized oligonucleotide illustrated in FIG. 3 in which the sequence that recognizes T790M and the sequence that recognizes C797S are bound to each other by the linker.

Each of the synthesized oligonucleotides of Table 4 was used as the template DNA and each of the probes (1) to (3) of FIG. 3 was used as the QProbe binding probe, and hybridization was performed by employing the following reagent composition. After mixing a screening master mix (30 mM KCl, 10 mM Tris-HCl (pH 8.0), 0.1% Tween, 1.6 µM synthesized oligonucleotide, 0.05 µM probe), in the real-time fluorophotometer LC480 (manufactured by Roche), the temperature of a resultant reaction solution was gradually increased (acquisition 7/° C.) from 37° C. to 80° C., and the fluorescence intensity was measured for performing the thermal melting curve analysis. As a result of the thermal melting curve analysis performed by measuring the fluorescence intensity, when the synthesized oligonucleotide of C797S-1 was used, the probe (1) alone most efficiently quenched, and thus, merely the sequence comprising T790M and C797S in the cis configuration could be detected. The results of the thermal melting curve analysis obtained by using the synthesized oligonucleotide in which the sequence that recognizes T790M and the sequence that recognizes C797S were bounded by the linker (TTTTTTT) illustrated in FIG. 3 are illustrated in FIG. 4.

Example 4: Detection of Cis Mutation by LAMP Method

The synthesized oligonucleotide of C797S-1 (SEQ ID NO: 3) by which merely the sequence comprising T790M and C797S in the cis configuration could be efficiently detected in Example 3 was converted into a probe to produce a linker probe for cis configuration detection.

Referring to the EGFR gene reference sequence of Example 1 and the mutations of Table 1, an EGFR gene sequence comprising T790M and C797S in the cis configuration, an EGFR gene sequence comprising T790M and C797S in the trans configuration, an EGFR gene sequence comprising T790M alone, and an EGFR gene sequence comprising C797S alone were designed to produce artificial genes.

Figure 5:
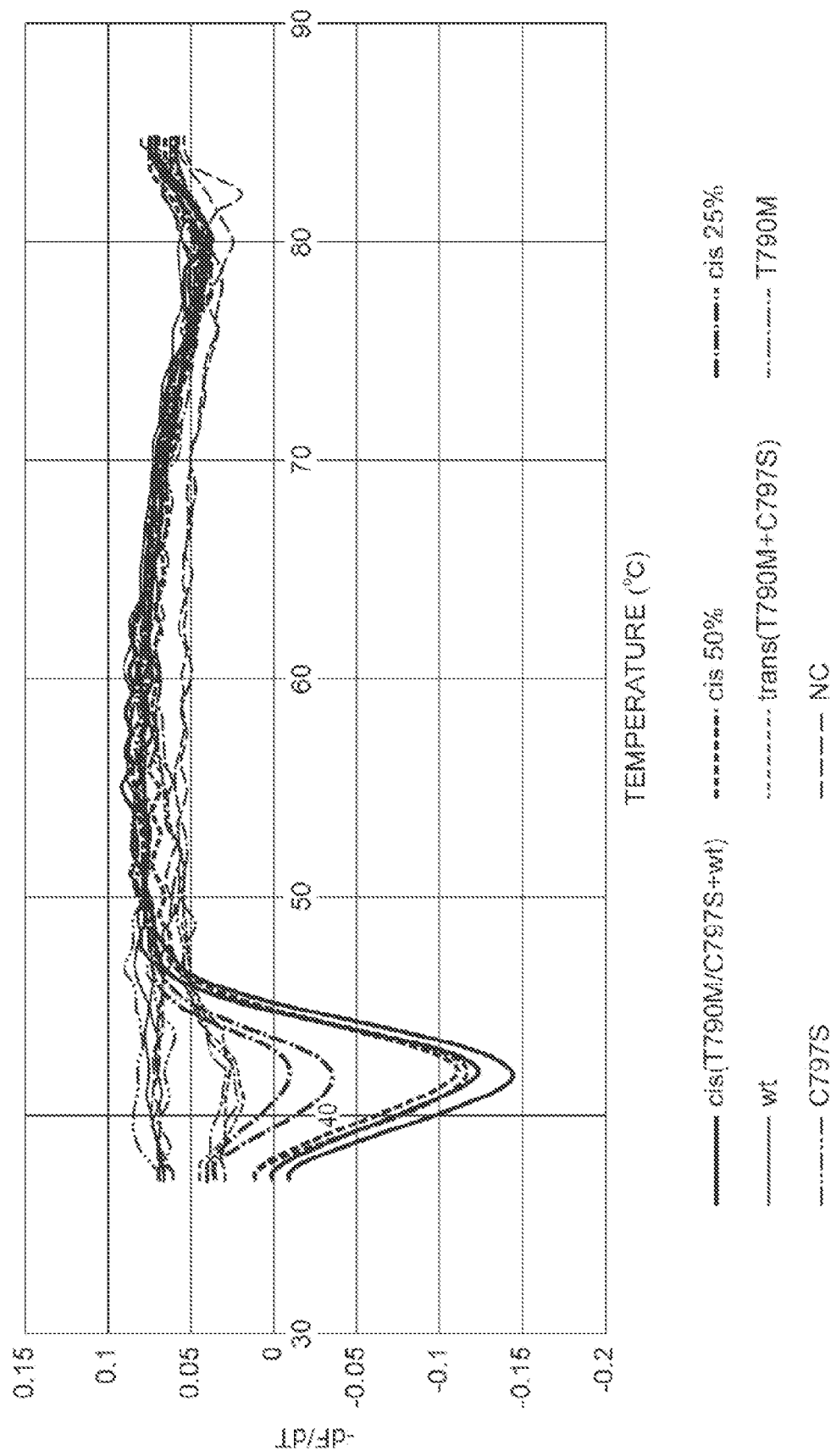
FIG. 5 illustrates results of thermal melting curve analysis obtained by using a linker probe for cis configuration detection. A curve of "cis (T790M/C797S+wt)" corresponds to a case where template DNAs include a DNA (T790M/C797S) having an EGFR gene sequence comprising T790M and C797S in the cis configuration, and a DNA (wt), used as an allele, not comprising the mutations and having the wild type EGFR gene sequence. Curves of cis50% and cis25% respectively correspond to cases where the template DNAs include DNAs respectively containing 50% and 25% of T790M/C797S (with the other DNAs being DNAs having the wild type EGFR gene sequence), and a DNA (wt), used as an allele, not comprising the mutations and having the wild type EGFR gene sequence. Accordingly, mutation ratios of T790M/C797S in the cases of cis50% and cis25% are respectively 25% and 12.5%. A curve of "trans(T790M+C797S)" corresponds to a case where all the template DNAs are DNAs having an EGFR gene sequence comprising T790M and C797S in the trans configuration, a curve of wt corresponds to a case where all the template DNAs are DNAs having the wild type EGFR gene sequence, a curve of T790M corresponds to a case where all the template DNAs are DNAs having an EGFR gene sequence comprising T790M alone, and a curve of C797S corresponds to a case where all the template DNAs are DNAs having an EGFR gene sequence comprising C797S alone.

Each of the artificial genes and a genomic DNA having a sequence of the wild type EGFR gene was used as the template DNA, the linker probe for cis configuration detection was used as the QProbe binding probe, and the hybridization was performed by the LAMP method in the same manner as in Example 2. Quenching slightly observed when the oligonucleotide having the sequence of the artificial gene comprising C797S alone was used was excluded, and for further improving sensitivity, 1.2 µM of a competing oligonucleotide (SEQ ID NO: 2) completely complementary to a wild type of a T790M sequence portion was added. Results of the thermal melting curve analysis of products of the LAMP method performed by measuring fluorescence intensities in the same manner as in Example 2 are illustrated in FIG. 5.

By using the linker probe for cis configuration detection, merely a case where T790M and C797S were present in the cis configuration could be detected. Besides, it was revealed that the detection can be performed up to a mutation content of 12.5%. Here, the term "mutation content" means a ratio of template DNAs comprising the mutation in the whole template DNAs.

The invention claimed is:

1. An oligonucleotide probe for single nucleotide polymorphism detection, for determining, in a target nucleic acid where a first single nucleotide polymorphism and a second single nucleotide polymorphism are present in different positions, whether the first single nucleotide polymorphism and the second single nucleotide polymorphism are present in a cis configuration or in a trans configuration, wherein the target nucleic acid comprises a first target sequence where the first single nucleotide polymorphism is present, and a second target sequence where the second single nucleotide polymorphism is present, the probe comprises a reporter region for detecting the first single nucleotide polymorphism, an anchor region for detecting the second single nucleotide polymorphism, and a linker region, the reporter region comprises an oligonucleotide consisting of a sequence perfectly matching with the first target sequence, and a fluorescent dye that quenches when the first target sequence and the reporter region hybridize, the anchor region comprises an oligonucleotide consisting of a sequence perfectly matching with the second target sequence, the linker region links the reporter region and the anchor region, and is an oligonucleotide consisting of 3 to 11 nucleotides and consisting of only one kind of base selected from adenine, guanine, cytosine and thymine, wherein the oligonucleotide of the linker region is non-complementary to a sequence disposed between the first target sequence and the second target sequence in the target nucleic acid when the first single nucleotide polymorphism and the second single nucleotide polymorphism are present in the cis configuration, and a length of the oligonucleotide of the reporter region is shorter than a length of the oligonucleotide of the anchor region.

2. The probe according to claim 1, wherein the linker region is an oligonucleotide consisting of a sequence comprising no universal base.

3. A method for determining whether a first single nucleotide polymorphism and a second single nucleotide polymorphism are present in a cis configuration or in a trans configuration, comprising:

preparing a mixture by mixing the probe according to claim 2, and a target nucleic acid where the first single nucleotide polymorphism and the second single nucleotide polymorphism are present in different positions;

measuring fluorescence intensity of the mixture; and determining, on the basis of the fluorescence intensity, whether the first single nucleotide polymorphism and the second single nucleotide polymorphism are present in the cis configuration or in the trans configuration.

4. A method for determining whether a first single nucleotide polymorphism and a second single nucleotide polymorphism are present in a cis configuration or in a trans configuration, comprising:

preparing a mixture by mixing the probe according to claim 1, and a target nucleic acid where the first single nucleotide polymorphism and the second single nucleotide polymorphism are present in different positions;

measuring fluorescence intensity of the mixture; and determining, on the basis of the fluorescence intensity, whether the first single nucleotide polymorphism and the second single nucleotide polymorphism are present in the cis configuration or in the trans configuration.

5. The oligonucleotide probe of claim 1, wherein the target nucleic acid is the epidermal growth factor receptor (EGFR).

6. The oligonucleotide probe of claim 5, wherein the EGFR is Homo sapiens EGFR.

7. The oligonucleotide of claim 6, wherein the first single nucleotide polymorphism causes a C797S mutation.

8. The oligonucleotide of claim 7, wherein the C797S mutation is caused by a 2389 T>A or 2390 G>C single nucleotide polymorphism.

9. The oligonucleotide of claim 6, wherein the second nucleotide polymorphism causes a T790M mutation.

10. The oligonucleotide of claim 9, wherein T790M mutation is caused by a 2369 C>T single nucleotide polymorphism.

11. The oligonucleotide of claim of claim 6, wherein the first single nucleotide polymorphism causes a C797S mutation and wherein the second nucleotide polymorphism causes a T790M mutation.

12. The oligonucleotide of claim 11, wherein the C797S mutation is caused by a 2389 T>A or 2390 G>C single nucleotide polymorphism and wherein T790M mutation is caused by a 2369 C>T single nucleotide polymorphism.

13. The oligonucleotide of claim 11, wherein the first and second nucleotide polymorphisms are in cis configuration.

14. The oligonucleotide of claim 13, wherein the fluorescent dye is quenched.

15. The oligonucleotide of claim 11, wherein the first and second nucleotide polymorphisms are in trans configuration.

16. The oligonucleotide of claim 15, wherein the fluorescent dye is not quenched.

* * * * *